United States Patent [19]
Renken

[11] Patent Number: 6,009,350
[45] Date of Patent: Dec. 28, 1999

[54] IMPLANT DEVICE TELEMETRY ANTENNA

[75] Inventor: Gerald W. Renken, Edina, Minn.

[73] Assignee: Medtronic, Inc., Minneapolis, Minn.

[21] Appl. No.: 09/019,912

[22] Filed: Feb. 6, 1998

[51] Int. Cl.$^6$ .................................................. A61M 1/362
[52] U.S. Cl. .............................. 607/32; 607/60; 128/903
[58] Field of Search ............................ 128/903; 607/32, 607/60

[56] References Cited

U.S. PATENT DOCUMENTS

| | | | |
|---|---|---|---|
| Re. 32,361 | 2/1987 | Duggan | 607/32 |
| 3,218,638 | 11/1965 | Honig | 128/903 |
| 3,683,389 | 8/1972 | Hollis . | |
| 4,026,305 | 5/1977 | Brownlee et al. . | |
| 4,267,843 | 5/1981 | McDonald . | |
| 4,273,133 | 6/1981 | Hartlaub et al. . | |
| 4,361,153 | 11/1982 | Slocum . | |
| 4,401,120 | 8/1983 | Hartlaub . | |
| 4,440,173 | 4/1984 | Hudziak et al. . | |
| 4,441,498 | 4/1984 | Nordling | 128/903 |
| 4,515,159 | 5/1985 | McDonald . | |
| 4,585,004 | 4/1986 | Brownlee | 607/32 |
| 4,809,697 | 3/1989 | Causey . | |
| 4,979,506 | 12/1990 | Silvian . | |
| 5,058,581 | 10/1991 | Silvian . | |
| 5,107,833 | 4/1992 | Barsness . | |
| 5,127,404 | 7/1992 | Wyborny . | |
| 5,137,022 | 8/1992 | Henry . | |
| 5,168,871 | 12/1992 | Grevious . | |
| 5,241,961 | 9/1993 | Henry . | |
| 5,292,343 | 3/1994 | Blanchette et al. . | |
| 5,324,315 | 6/1994 | Grevious et al. . | |
| 5,344,431 | 9/1994 | Merritt et al. . | |
| 5,350,411 | 9/1994 | Ryan et al. . | |
| 5,354,319 | 10/1994 | Wyborny . | |
| 5,562,714 | 10/1996 | Grevious . | |
| 5,569,307 | 10/1996 | Schulman . | |
| 5,693,076 | 12/1997 | Kaemmerer . | |
| 5,697,958 | 12/1997 | Paul et al. | 607/60 |
| B1 4,373,527 | 2/1983 | Fischell . | |

*Primary Examiner*—William E. Kamm
*Assistant Examiner*—George R. Evanisko
*Attorney, Agent, or Firm*—Harold R. Patton; Michael B. Atlass

[57] ABSTRACT

An antenna apparatus for an implantable medical device is adapted and disposed to have an increased telemetry range by providing a plurality of antennas connected in parallel with each other, and physically separated from each other. The antennas may be mounted within the IMD can or they may be located externally, outside the IMD can, but associated and mounted to the IMD can package. The antennas may have coils wound around an air-core or a non-air core such as ferrite. There can be any number of them but it is preferably a number between 1 and 10.

17 Claims, 5 Drawing Sheets

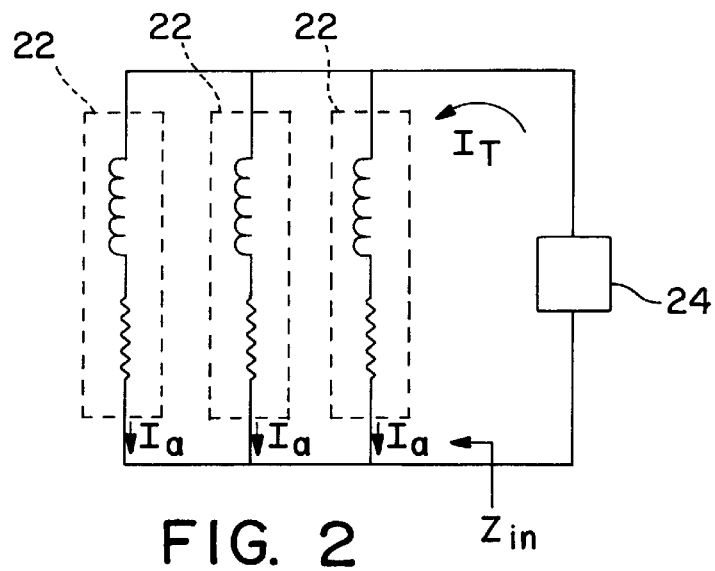
FIG. 2
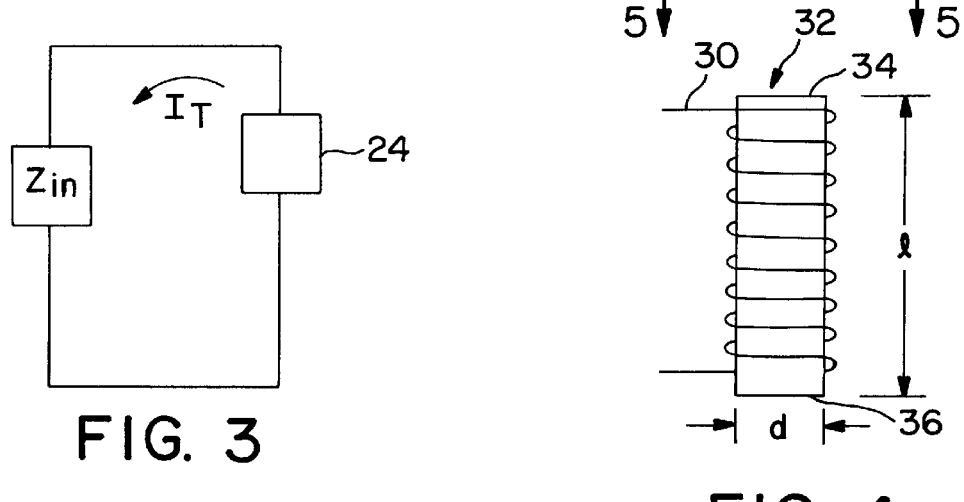
FIG. 3
FIG. 4

IMPLANT DEVICE TELEMETRY ANTENNA

FIELD OF THE INVENTION

The present invention relates generally to the field of implantable medical devices. More particularly, it relates to telemetry systems for implantable medical devices.

BACKGROUND OF THE INVENTION

Since the advent of implantable medical devices, the fields of medicine and electronics have advanced significantly. Accordingly, both the variety and availability of implantable medical devices have increased rapidly. Implantable medical devices to which this invention could be applied currently include not only pacemakers, but also defibrillators, neural stimulators, drug and other therapy delivery systems, monitoring devices some having implanted sensors, and implantable cardioverters, and combinations of these devices, among others.

Early implantable devices were non-invasively controlled to perform simple functions such as turning the device on or off, or adjusting a fixed pacing rate, and even some reporting out of data. These early devices commonly used a magnetic reed switch as a simple telemetry control device. The reed switch could be opened or closed by a magnet held to the patient's skin over the implanted device. In this manner, using the reed switch, the implanted device could be turned on or off. Fixed pacing rates could also be adjusted, for example, by the amount of time the reed switch remained closed, or the number of times it was closed and opened in a given period or a rate or openings and closings, for examples. Such controls, using the reed switch, allowed only for very basic transmittal of signals to implanted devices, and were very limited in function.

As implantable medical devices became more and more sophisticated, the amount of information desired to be transmitted to (and from) the implanted devices grew. Using pacemakers as an example, these functions include switching the device operation into different operating modes, and varying the pacing energy levels delivered to the heart. Pacing rates, device calibration information, and other device parameter settings, and even programming differing therapies and monitoring different body conditions or changing the type of monitoring behavior can also be included in a list of items alterable by and employing the telemetry function. Due to the need to communicate increased amounts of information to implanted medical devices, reed switches became insufficient to adequately perform programming and control functions. As implantable medical devices increased in complexity, it also became desirable for an external programming unit to be able to receive more and better information transmitted by the implanted device. Information that is desirable to be received from an implanted device may include operational status information, information sensed by the implanted medical device such as ECG signals for analysis by a physician, and the like.

There are many telemetry systems that have been used or have been disclosed and these include disclosures on various aspects of such systems particularly suited to implantable devices they are described with reference to in the following U.S. Pat. Nos., which are hereby incorporated by reference:

4,026,305; Brownlee et al., Low Current Telemetry System For Cardiac Pacers
4,267,843; McDonald et al.; Means to Inhibit a Digital Cardiac Pacemaker
4,273,133; Hartlaub et al; Programmable Digital Cardiac Pacemaker with . . .
4,361,153; Slocum et al; Implant Telemetry System
4,373,527; Fischell; Implantable, Programmable Medication Infusion System
4,401.120; Hartlaub et al.; Digital Cardiac pacemaker with Program Acceptance Indicator
4,440,173; Hudziak et al.; Programmable Body Stimulation System
4,515,159; McDonald et al.; Digital Cardiac Pacemaker with Rate Limit Means
4,809,697; Causey, III et al.; Interactive Programming and Diagnostic System for Use With Implantable pacemaker
4,979,506; Silvian; Self-Test System and Method for External Programming Device
5,058,581; Silvian; Telemetry Apparatus and Method for Implantable Tissue Stim . . .
5,107,833; Barsness; Telemetry Gain Adjustment Algorithm and Signal Strength Indication in a Noisy Environment
5,127,404; Wyborny et al., Telemetry Format for Implanted Medical Device
5,137,022; Henery; Synchronous Telemetry System and Method for an Implantable . . .
5,168,871; Grevious; 5,168,871; Method and Apparatus for Processing Quasi Transient Telemetry Signals in Noisy Environments
5,241,961; Henry; Synchronous Telemetry Receiver and Receiving Method for an Implantable Medical Device
5,292,343; Blanchette et al.; Hand Shake For Implanted Medical Device Telemetry
5,324,315 Grevious; Closed Loop Downlink Telemetry and Method for Implantable Medical Device
5,344,431; Merritt et al., Method and Apparatus for Determination of End-Of-Service For Implantable Devices
5,354,319; Wyborny, et al., Telemetry System for an Implantable Medical Device
5,350,411; Ryan et al.; Pacemaker Telemetry System
5,562,714; Grevious; Magnetic Field Strength Regulator for Implant
5,569,307 Schulman et al.; Implantable Cochlear Stimulator having Backtelemetry Handshake Signal
5,693,076; Kaemerer; Compressed Patient Narrative Storage and Full Text Reconstruction From Implantable Medical Devices The above-mentioned patents are all incorporated hereinto by this reference. They describe telemetry problems and solutions that run the gamut from dealing with reed switch/device interaction, to protocol for communicating via telemetry, to assisting in the programming of the device, to making adjustments for signal strength. While the list is not exhaustive it is believed to roughly represent the state of the art. Of most relevance to this invention are the ones concerned with adaptation to signal strength, but the others do provide useful background. For this invention we are most concerned with antenna configuration and use, and the prior art in this area is not well developed for the implantable device field.

Typical telemetry systems for implantable medical devices operate with a radio-frequency (RF) transmitter and receiver in both the device and in the external programming unit. The device transmitter and receiver typically use a wire coil element for receiving telemetry signals. The telemetry signals are received from a hand held programming head which is connected to the programming unit, and which is positioned over the implant site in close proximity to the implant. The device transmitter communicates signals to the external programming unit through the programming head. Signals transmitted to the implantable medical device in this fashion are referred to as downlink or downlink telemetry. Signals transmitted from the implantable medical device to the external unit are referred to as uplink or uplink telemetry. The usable uplink range of implantable medical devices is usually quite limited due to the small current amplitudes that the uplink transmitters have to work with.

Implanted medical devices typically have an internal battery(although tapping into body provided energy sources is not unheard of), which provides a power source to drive the normal operative functions of the implanted medical device. When a telemetry session is initiated, this battery must also provide power to operate the RF uplink and downlink telemetry circuitry within the device. This battery has an output terminal voltage, which is limited to a small value of typically 2 or 3 volts. Charge pumping a capacitor can alleviate some of this limitation, but the inventor believes that would be a more costly solution and in any event is not discussed here. During the telemetry system, the battery must also supply a DC current from its terminal voltage to continue the normal implanted device circutry operations.

The power delivered from the battery is calculated as the product of the battery's terminal voltage multiplied by the current delivered from the battery. Since the normal operating functions of the internal medical device circuitry cannot be compromised during a telemetry session, the battery power taken to operate the telemetry circuitry must be limited. The telemetry transmitter and the normal operating functional circuitry both operate at the same battery terminal voltage. Consequently, the only way to restrict the battery power consumed for telemetry is to restrict the amount of current used by the telemetry transmitter and its coil antenna.

The amount of battery current taken for telemetry, while minimized, cannot be set to an arbitrary small value because the telemetry system must also operate over a specified minimum uplink range. In general, from the perspective of this invention, the larger the sweet spot that can be provided with the same amount of battery (or other) current, the better.

The range over which a telemetry link provides acceptable signal transfer, especially for the uplink from the implantable device to the programmer is a key factor in the telemetry system design. Other factors being equal, range depends upon the current amplitude delivered to the coil antenna. Any limitation on the amount of current supplied to the IMD telemetry transmitter and coil antenna will directly limit the telemetry uplink range unless the current is used efficiently within the transmitter and coil antenna. The greater the telemetry transmitter and coil antenna current, the greater the telemetry uplink range becomes, at the expense of less current available for the IMD circuitry.

For our purposes, we prefer to do telemetric communication from our implanted device using the near H field from the coil antenna rather than the E field. This is because the H field wave impedance is much less than it is for E field wave impedance, allowing lower loss signal transmission through the metal can which usually forms the shell of the implanted device, and through the flesh and skin. (The near field is generally considered to be less than 1/6th of the wave length of the carrier wave.) Therefore, in our preferred telemetry, uplink telemetry range depends upon the near field magnetic field strength or amplitude for our preferred embodiments. (For devices ata a range close to the body, or having more uplink transmitter power, or with antenna(e) outside of a metal capsule or shell, the E field may be used as well, and then, the electric field strength would be the limiting factor with respect to range. There are other problems with regulatory authorities when using E fields, another reason we prefer the H field as the data transmission vector).

The magnetic field strength depends on the number of coil turns in the antenna, the area of the coil, and the coil current. The uplink transmitter efficiency depends on the coil quality factor, Q. To increase the telemetry uplink range, the magnetic field intensity must be maintained at an increased distance from the implanted device. The magnetic field may be increased by: adding more turns to the coil; making the coil antenna larger in area, winding it with a larger radius; or by driving the coil with a larger coil current. The larger the coil Q, the more efficient the uplink transmitter circuit becomes It should be noted that, for either uplink or downlink, it would be desirable to utilize only near-field magnetic fields (H fields), which do not require federal licensing since their amplitude falls off so rapidly with link range. Second, it would be desirable to use these near-fields with the within described inventive coil antenna implementation to increase the uplink range of the telemetry by maximizing the transmitted magnetic field strength. This inventive antenna implementatioin provides this range increase by directly dealing with the problem of the limited fixed voltage supplied by the implantable device's battery.

For a fixed coil voltage, adding more turns to the coil will increase the magnetic field intensity generated by the coil. Unfortunately, adding more turns to the coil will increase the coil's self-inductance and its associated input reactance with the result that less current can then be driven into the coil. The resulting coil drive current is then limited because of the fixed (battery) voltage since the coil antenna's inductance and therefore its inductive reactance increase correspondingly with the number of turns in the coil. The magnitude of current flowing in the coil is equal to the battery voltage divided by the inductive reactance of the coil antenna. Therefore, for a fixed coil voltage, adding more turns to the coil actually results in reduced coil current and smaller magnetic field intensity.

Coil antennas with larger areas may be used to increase the magnetic field intensity. The ideal coil antenna design for uplink applications would have an area as large as can be accommodated, either within, or external to the Implantable Medical Device(IMD) can. Unfortunately, the area of the coil antenna is usually not arbitrary. The coil must be small in area to fit within the volume allotted to it by the overall IMD configuration. The coil antenna should have as large an area as possible in order to produce a large uplink sweet spot. Coil antennas with larger areas produce larger sweet spot volumes. The physical configuration of the antenna essentially determines the sweet spot radius and associated volume.

The sweet spot, at a specified range, for uplink telemetry is defined to be a volume above and adjacent to the site of an implanted medical device. Within the sweet spot volume, at the range specified, the telemetry signal voltage received by the external communicating or programming head equals or exceeds a specified value. The received signal voltage is generated by the time varying magnetic flux density within the sweet spot. (The specified value of signal voltage is defined to be an amplitude greater than the lower limit of signal voltage amplitude the expected to be used for reception of the signal). Larger sweet spot volumes are desired in medical telemetry because placement of the programming head within a large volume is simple to acheive and in an operating room or clinical environment. Thus placement of the programming head relative to the implanted device location will not be critical to maintain a strong telemetry uplink signal, because of the relatively large sweet spot volume acheivable with this invention.

The IMD coil antenna should have a Q as large as possible in order to maximize transmitter efficiency. Too large a Q value will also limit the IMD transmitter's 3-dB bandwidth (BW). For a specified transmitter signal bandwidth, the coils' loaded in-circuit Q is defined as, Q=F/BW, (where F is frequency). The loaded, in-circuit coil Q must provide the required signal bandwidth or some of the transmitted uplink telemetry signal power will be lost. So there are limitations to be placed upon the loaded Q value for the IMD coil antenna. Its in-circuit, loaded Q cannot be made arbitrarily large without directly impacting the transmitter signal bandwidth.

The current made available for telemetry is limited by two factors. First, the limited battery voltage available for a telemetry transmitter and coil antenna in an implantable medical device limits the current available to drive the telemetry circuitry. Second, as explained above, the inductive reactance of the coil antenna will limit coil antenna input current. For a fixed voltage driving the coil antenna, at a fixed frequency, as the coil's inductive reactance increases, the coil's input current is reduced. Also, as the life cycle of the IMD battery progresses, the internal resistance of the battery increases. This increased internal resistance further limits the current available from the battery to drive the antenna coil, since the effect of increased internal resistance is to reduce the available terminal voltage from the battery.

A number of potential solutions to the problems of increasing uplink telemetry range, but which do not involve increasing the coil current have been proposed. These methods however have not proven effective.

Larger inductor coil areas would increase the uplink range when driven by small telemetry currents, but usually are not feasible given the small area allotted to the coil in an implantable medical device. The space allocated for the telemetry circuitry and its associated coil antenna is often limited by the volume remaining after the device circuit components (and the battery) have been placed within the implant can.

An increased number of coil turns would provide a larger magnetic field strength to carry the telemetry signals further. However, since the IMD battery voltage is fixed more coil turns will actually limit the coil current because an increased number of coil turns increases the coil's self inductance, and the inductive reactance of the coil antenna, thereby limiting the coil current.

The loaded coil Q factor should also be maintained at the highest possible level to improve transmitter efficiency, but its value must be consistent with maintaining the specified uplink signal bandwidth.

Given the relatively small volume allotted to the coil antenna, fixed battery terminal voltage, self inductance and inductive reactance limitations of the present telemetry antenna technology, it would be desirable to increase the coil transmit current while maintaining the coil quality factor while remaining within size constraints imposed by implantable medical device cases, to increase the uplink telemetry range. The prior art has not provided an acceptable solution for increasing the telemetry range of an implantable medical device.

BRIEF SUMMARY OF THE INVENTION

The present invention overcomes the problems of the prior art by providing an implantable medical device with an increased uplink telemetry range, utilizing a plurality of identical electrical elements such as coil antennas connected in parallel to increase current flow in the telemetry circuitry without compromising the medical or operative functions of the device, and without exceeding space limitations imposed by the size of the device.

The increased telemetry range antenna configuration comprises a plurality of identical coil antennas connected in parallel and spaced apart from each other. The parallel connection of the coil antennas decreases the effective input impedance of the configuration by a factor of N, with N being the number of identical coils connected in parallel. For a single coil antenna having a coil inductance of $L_s$, a coil winding loss of $R_s$, and an input impedance of $Z_{in}$, the coil current $I_{in}$ is equal to the battery voltage ($V_{Tx}$) divided by the input impedance of the coil antenna, $I_{in}=V_{Tx}/Z_{in}$. Telemetry range depends upon magnetic field intensity H, where H is defined by the equation:

$$H = \left\{\frac{kN_S A Q_S I_{in}}{R^3}\right\}, Q_S = \left\{\frac{\omega L_S}{R_S}\right\}, \text{ and } \lambda = \frac{c}{F}$$

where: c=velocity of light in freespace, $c=3.0\times10^8$ meters/sec.

$N_s$ is the number of turns in the coil,

A is the coil area in square meters,

F=signal frequency in Hertz, $\lambda$=freespace wavelength in meters $Q_s$ is the coil's in-circuit loaded quality factor $R_S$ is the total in-circuit loss seen by the coil $I_{in}$ is the coil current in amperes, and R is the link range in meters.

To increase telemetry uplink range, the same magnetic field intensity H must be provided at an improved range as is provided at the original range. The coil in-circuit, loaded quality factor, any constants, the number of turns in the coil, and the coil area are substantially fixed due to the constraints and problems described above. Therefore, to increase the range R by maintaining magnetic field strength, coil current must be increased.

The common antenna configuration used in implantable medical devices today typically utilizes a single coil antenna driven by the internal battery. This antenna configuration has an associated input impedance $Z_{in}$. The input coil current in the circuit, $I_{in}$, is controlled by the equation $I_{in}=V_{Tx}/Z_{in}$, where $I_{in}$ is the current and $V_{Tx}$ is the battery terminal voltage. A telemetry circuit with an electrically parallel configuration of N identical coils will have an equivalent input impedance of $Z_{in}$ divided by N. The calculation of such input impedance associated with a parallel combination is well known and will not be discussed further. With a constant battery terminal voltage, $V_{Tx}$, if the impedance falls, the current in the entire circuit will rise. The current in each coil leg(that is each spaced apart coil that together form the overall antenna configuration, here assumed to be "identical) of the parallel combination will remain what it would be if the coil were the only coil(in other words, just a single coil leg), but the total current, which is the important factor for the total magnetic field strength, will be the sum of the currents through the individual coils. (A short discussion of 'identicalness' of coil legs follows later. For now, it is sufficient to say that any number greater than one leg could be used but preferrably less than 10 or 6 or some small number would be used to keep the design somewhat simple).

Due to the space considerations in many of today's implantable medical devices, the need has arisen for smaller area coils. However, the use of a single smaller area coil will affect uplink range. However, the use of several smaller coils connected in parallel will allow the input current to the coil set to be increased, and yet still account for these space constraints. In order to create the optimal uplink telemetry volume, or sweet spot, multiple identical coils connected in parallel are equally spaced apart within the volume associated with the implantable medical device. As a result, their individually generated magnetic fields will overlap to create a larger telemetry volume, or sweet spot, for the multiple antenna configuration. Since the coils of such a parallel configuration are smaller than traditional larger coils used in implantable medical devices, it has been found that an arrangement in which the multiple coils are spaced apart equally around the perimeter of the implantable medical device creates the most consistent and largest field. The coils may be spaced apart equally around the inside perimeter or theoutside perimeter of the medical device metal can.

To concentrate the field further when forced to use a smaller area coil, a coil core material such as ferrite to replace the air core may be used. Just as for air core coils, the magnetic field from a ferrite core also radiates from each end of the core, longitudinally. Due to the position of implantable medical devices within the body of a patient, that is with the largest area substantially parallel to the patient's skin, the thin width of an implantable medical device is substantially perpendicular to the patient's skin. Therefore the long dimension of the core must be aligned along the thickness of the implanted medical device to take advantage of the longitudinal orientation of the ferrite core field radiation effect. Because of the nature of the magnetic field in a ferrite core, a demagnetization effect uponof the ends of the ferrite rod requires that the length to diameter ratio of a ferrite core rod be at least five to one. This length to diameter requirement, coupled with the small thickness of a typical implantable medical device means that the cross-sectional area of a typicalferrite rod coil antenna used in an implantable medical device is quite small. Because of the associated small sweet spot area for one ferrite rod antenna, a multiple antenna configuration enlarges the overall field by allowing the multiple antennas to create an overlapping field pattern. A larger air core antenna could supply the same sweet spot as a correspondingly smaller ferrite core antenna, but the general problem with implantable device is space (i.e. volume) constraints, as already discussed.

Another consideration with respect to the use of multiple coils is the coil in-circuit loaded quality factor, $Q_l$. The coil quality factor is important because it preserves the signal bandwidth of the implantable pulse generator using an antenna. The coil quality factor depends on the radian frequency at which the antenna is driven, the coil inductance, and the coil winding loss. It is desirable to have a coil quality factor as high as possible, consistent with the link signal bandwidth, in order to use the limited amount of voltage available for driving the antenna most efficiently. The use of identical small coil antennas preserves the overall coil quality factor, since each coil has the same $Q_l$. The total coil quality factor of $Q_T$ a combination of parallel coils is the same as the quality factor $Q_l$. for one coil, provided the coils are identical. The parallel combination of coils allows the driving of the uplink transmitting antenna with a limited voltage while still allowing the maintenance of the same signal bandwidth and transmitter efficiency. To the extent that the coils (or coil legs) are not identical, the bandwidth (BW) will decrease, however, this invention can be used with nonidentical coil legs, or substantially identical coil legs to varying degrees of efficaciousness.

Having maintained the same magnetic field intensity at a larger range by increasing the current through the coil, the uplink range increase with a fixed battery voltage will be by a factor of the cubed root of the number of identical coils connected in parallel. Considerations of space, weight, and expense will necessarily limit the number of coils that may be connected in parallel.

These and other objects and benefits of the present invention will become apparent from the following detailed description thereof taken in conjunction with the accompanying drawings, wherein like reference numerals designate like elements throughout the several views.

DESCRIPTION OF THE DRAWINGS

FIG. 2 is a circuit diagram of an embodiment of the antenna configuration of the present invention;

FIG. 3 is a diagram of an electrically equivalent circuit to that shown in FIG. 2;

FIG. 4 is a vertical elevation view of an antenna coil and core;

DESCRIPTION OF THE PREFERRED EMBODIMENTS

Figure 1:
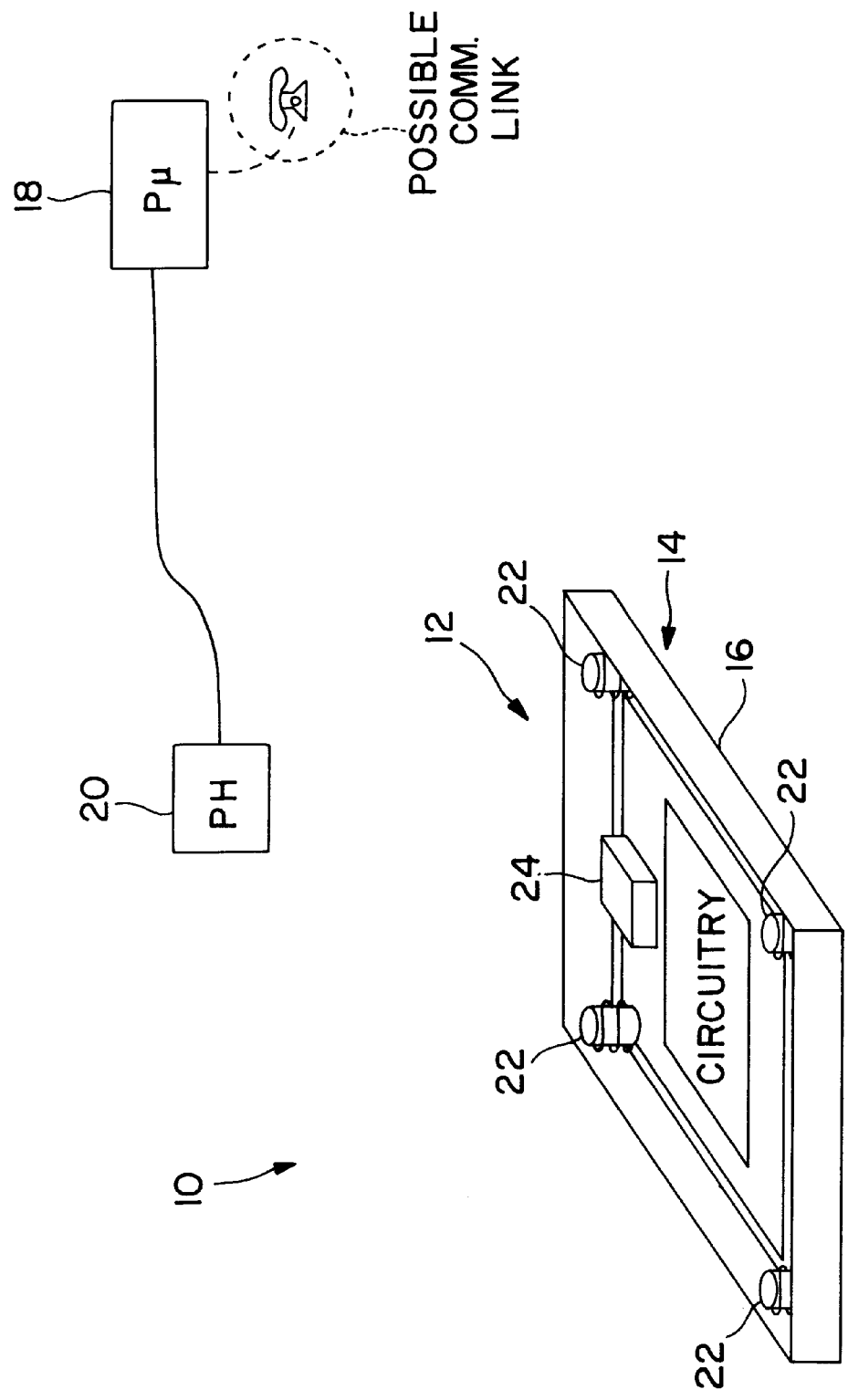
FIG. 1 is an isometric view of a typical implantable medical device and a programming unit and head.

Referring now to the drawings, and especially to FIG. 1, the increased range antenna apparatus 10 may be seen in place on a typical implantable medical device (IMD) 12. Antenna apparatus 10 is part of an implantable pulse generator (IMD) 14 which has its circuitry disposed within an implantable pulse generator case 16. The IMD 14 is in turn implanted into a patient's body at an appropriate location, which will depend upon the function of the device. Implantable medical device 12 also comprises an external programming unit 18 and a programming head 20 operatively connected thereto. The programming head 20 includes an antenna, a downlink radio frequency (RF) transmitter, and an uplink RF receiver. Programming head 20 is used to send downlink telemetry to and receive uplink telemetry from, the telemetry components of IMD 14. The functions and specific components of a typical implantable medical device are disclosed in the following United States Patents, owned by the Assignee of record for the present application, which are hereby incorporated by reference in their entirety:

The increased uplink telemetry range antenna apparatus 10 comprises a plurality of individual electric elements 22 such as coil antennas arranged so as to be spaced apart and connected in parallel with a power generation unit such as an IMD battery 24. IMD battery 24 produces a predetermined and set amount of voltage, $VT_{Tx}$. Each individual antenna 22 has an associated coil inductance $L_s$ and a coil winding loss $R_s$, and therefore an input impedance $Z_{in}$ of $Z_{in}=R_s+j\omega L_s$, where $\omega=2\pi F$ or $2\pi$ times signal frequency (F).

The voltage $V_{Tx}$ will cause a current $I_{in}$ to flow in the antenna apparatus 10. Since the individual antennas 22 are identical, the current through each antenna, $I_a$, will be identical. However, the total current $I_{in}$ flowing in the circuit will be the sum of the individual currents $I_a$ for N individual identical antennas 22, $I_{in}=N\ Ia$. The configuration of N identical antennas 22 arranged in parallel with voltage source $V_{Tx}$ is shown using N=3 in FIG. 2. The circuit representation of three antennas 22 as shown in FIG. 2 can also be represented by the equivalent circuit diagram shown in FIG. 3. In FIG. 2, $$Z_{in\_N} = \frac{R_S}{N} + j\frac{\omega L_S}{N} = \left(\frac{1}{N}\right)(R_S + j\omega L_S) = \frac{Z_{in}}{N}$$

for a constant IPG battery 24 voltage $V_{Tx}$:

$$I_{in} = \frac{V_{Tx}}{Z_{in\_N}} = N\frac{V_{Tx}}{Z_{in}}$$

As may be seen, the use of N individual antennas 22 provides an N-fold increase in the total current $I_T$ flowing in the circuit for a given constant battery voltage $V_{Tx}$. Uplink telemetry range, R, is determined by a number of factors. To increase the range, the magnetic field intensity, H, must remain at a level equal to that of the original range as it would be for an increased range.

The amplitude of the magnetic field intensity, H, (in amperes/meter) is governed by the equation:

$$H = \left\{\frac{kN_SAQ_1I_{in}}{R^3}\right\}, Q_1 = \left\{\frac{\omega L_S}{R_S}\right\}, \text{ and } \lambda = \frac{c}{F}$$

F=signal frequency in Hertz, $\lambda$=freespace wavelength in meters $N_S$ is the number of turns in the coil, $k=2\pi/\lambda$=Freespace wave number A is the coil area in square meters $Q_l$ is the coil's in-circuit loaded quality factor $R_S$ is the total in-circuit loss seen by the coil $I_{in}$ is the coil current in amperes, and R is the link range in meters.

For purposes of defining the total current input to the coil antenna we define the input current to each antenna to be $I_{in}$. As has been discussed above, each antenna 22 should be identical to allow the overall quality factor $Q_T$ to be identical to the quality factor $Q_l$ of each individual coil 22. Since k, $Q_l$, $N_S$, and A are limited in adjustability or are fixed due to the factors discussed above, an effective improvement in range will require an increase in total current input, $I_T$, to the set of antenna coils connected in parallel.

For example, at range, $R_i$, if the initial magnetic field strength, $H_i$ is:

$$H_i = \left\{\frac{kN_SAQ_1I_{in}}{R_i^3}\right\}$$

and $H_f$ the final magnetic field strength at range $R_f$ is:

$$H_f = \left\{\frac{kN_SAQ_1I_T}{R_f^3}\right\}$$

then for equal field intensities at the initial and final ranges $R_i$ and $R_f$, $H_i$ must equal $H_f$. In that case, taking the ratio of the equations for $H_i/H_f$ and canceling the same parameters in the ratio, we are left with: $I_i/R_i^3=I_T/R_f^3$. But since $I_T=N\ I_{in}$, where N equals the number of antennas 22 connected in parallel: $N\ R_i^3=R_f^3$; or, $R_f=\sqrt[3]{N}\ R_i$. For the case where N=3 antennas 22: $R_f=\sqrt[3]{3}\ R_i$; $R_f=R_i\ 1.44$.

Therefore, for three antennas 22 connected in parallel, the improved uplink telemetry range will be approximately 1.44 times the initial range for the same magnetic field intensity. The number of antennas to be arranged in parallel is chosen by considerations of the desired range increase and the space considerations in the IMD case 16. The greater the number of antennas, the greater the range increase.

Figure 7:
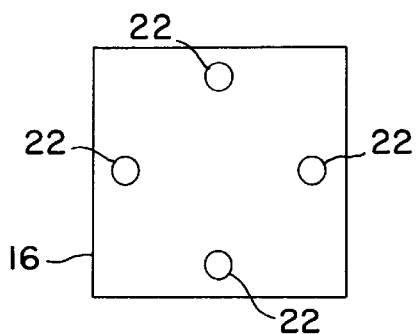
FIG. 7 is an alternative configuration of the antenna coils embodied in the present invention.
Figure 8:
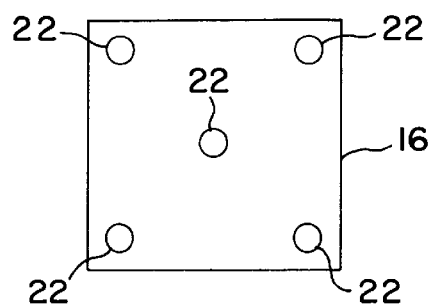
FIG. 8 is yet another alternative embodiment and antenna coil configuration embodied by the present invention.

Range alone, however, does not dictate the configuration or arrangement of antennas 22 in IMD case 16. Each antenna 22 has an associated field pattern, resulting in a corresponding telemetry uplink sweet spot volume. Compared with a single antenna 22, the parallel combination of antennas 22 will also provide an increased sweet spot volume. The increased sweet spot volume will depend upon the overlapping magnetic fields of the parallel antennas 22. Accordingly, the physical arrangement of antennas 22 within IMD case 16 becomes important. For a uniform sweet spot volume, the antennas 22 should be equally spaced apart. Examples of antenna configurations are shown in FIGS. 6–8.

Figure 6:
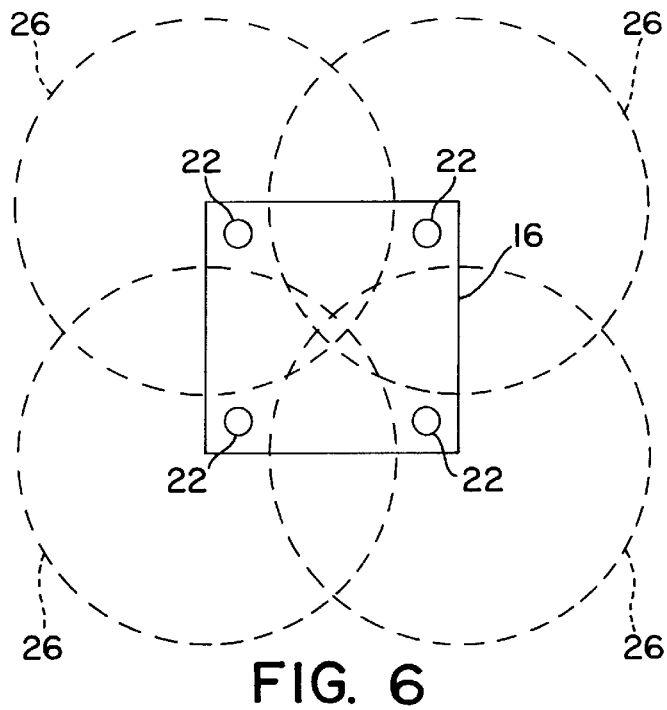
FIG. 6 is a partial top view of an implantable medical device showing a coil configuration embodied by the present invention.

An approximate field pattern for each antenna 22 is shown in FIG. 6 by dashed line 26. The total field pattern is the union of the individual field pattern. Considering only one coil, as the area of the coil is made smaller to accommodate the space constraints imposed by the IMD 14, the associated generated field pattern will necessarily decrease in size. As can be seen from FIG. 6, when several coil antennas are driven in parallel, the overlapping fields of the uniformly spaced antennas 22 provide a larger field pattern and larger sweet spot volume than each individual antenna 22 could provide on its own.

Figure 9:
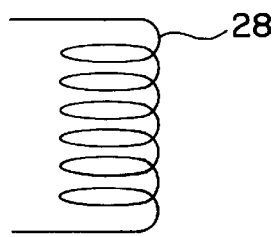
FIG. 9 is an isometric view of an air-core coil antenna.

The size of typical IMD cases such as case 16 varies depending on the specific implantable medical device and its purpose, but such a case is only large enough to contain the necessary circuitry and components. As technology has improved, components and therefore cases have decreased in size accordingly, both in thickness and in circumference. As a consequence, the front wall to back wall thickness for the newer IMD cases is often on the order of one-quarter inch or less. With the thinner IMD cases it is still possible to use small area coils wound around air. Such a coil 28 is shown in FIG. 9. However, with a small coil diameter, and an air core, the resultant field strength will be reduced due to the coil area reduction, hence the use of several air core antennas driven in parallel.

Figure 5:
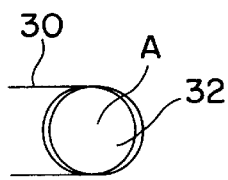
FIG. 5 is a view of the coil of FIG. 4 taken along lines 5—5 thereof.

For the same physical coil radius, the use of the proper core material other than air would allow the magnetic field generated to be increased or concentrated due to the properties of the coil core material. An example of a coil 30 wound around a non-air core 32 is shown in FIGS. 4 and 5. Preferably, the coil core 32 chosen will increase the field intensity compared to the air core coil. The preferred material for to be used as a core 32 is ferrite. Ferrite, when used as a core, will increase the concentration of the field generated by the antenna by a factor of 20–25. This concentration of the field allows the use of a coil antenna with a smaller volume and a correspondingly smaller area than an air core coil to be utilized in the IMD.

However, due to material characteristics of a ferrite core, certain size limitations in coil area must be imposed. Because of the characteristics of the ferrite, a minimum length (1) to diameter (d) ratio for the ferrite core must be maintained. This length to diameter ratio should be at least 5:1. At a length to diameter ratio of less then 5, the ability of a ferrite core to increase the magnetic field intensity within the core will be overcome by demagnetization.

The magnetic field radiates from the ends 34 and 36 of the ferrite rod 32, so the rods must be placed with their longitudinal length along the quarter inch thickness of the IMD case 16. With a required length to diameter ratio of 5:1 or greater in order to provide a ferrite rod that will be able to effectively concentrate the magnetic field. This necessarily creates an antenna area which is very small since the length, (1), must be less than the thickness of the case. Accordingly, the material chosen for the core 32 must be sufficient to concentrate the field. Ferrite has been found to be the preferred core substance due to the amount of field concentration it provides. The concentration of the magnetic field and the resultant small area coil antennas 22 allows the remaining circuitry of the implantable medical device 14 to occupy the majority of the space in the IMD case 16.

Because of the small telemetry core sizes, and the accompanying small area antennas 22, the sweet spot for the generated field of the implantable medical device will be maximized by the spaced apart placement of the parallel connected antennas 22. Further, when the antennas 22 are spaced apart, the interference between antennas, as well as the circuitry of the implantable medical device, and the medical components thereof, will be substantially reduced.

FIGS. 6–8 show various placement patterns for typical antennas 22 embodying the principles of the present invention. For example, FIG. 6 shows four identical antennas 22 arranged so that each antenna is separated by the maximum amount of distance from each other antenna, the placement having each antenna in a respective corner of the rectangular IMD case 16. The associated individual fields of the antennas 22 are shown by dashed lines 26. The area within the dashed lines 26 shows the total sweet spot for the configuration. Similarity, FIGS. 7 and 8 show alternate arrangements of parallel antennas. The arrangements are designed to maximize the sweet spot volume for the antenna coverage, and to minimize electrical and physical interference of the antennas with the remaining circuitry in the implantable medical device 14.

The telemetry of an implantable medical device is carried by a time varying magnetic field. The magnetic field used with implantable medical devices such as those discussed herein use the near-field magnetic field of the coil antenna. The near-field does not propagate, but couples the time-varying magnetic field energy from the transmit coil to the intended receive coil using magnetic induction. The amplitude of the near-field magnetic field falls off proportionally to the cube of the range. For example, at a double range, the field amplitude will only be one-eighth of the original amplitude. Implantable medical devices of the type embodying the present invention typically use the inductive near-field. Because of the ability of the present invention to be applied with near-field use, the implantable medical device embodying the present invention will not need to be licensed for FCC purposes.

The use of the antennas and the parallel antenna configuration described above apply equally well for air core or for other core antennas. For both coil antennas, the number of coil turns and if selected, the choice of specific ferrite for the core may be made to generate the appropriate field size and strength for the telemetry required. Such choices are well known within the art, and greater detail will not be provided herein.

The concepts of the present invention, although described with respect to standard titanium IMD cases 16, apply equally well with other types of cases, including ceramic. In the case of different choices of materials to be used for IMD case 16, various shields may be required to be used. For example, with a ceramic case, a shield to block electric fields would be required. Such shielding is known in the art, and will not be discussed further therein. The principles and disclosure of the present invention also apply equally well for antennas housed within an IMD or other enclosures, metallic or non-metallic, or for antennas located in a free space environment. While near-field use is preferred due to licensing considerations, the principles of the invention apply equally well for the antenna signal region as the reactive, non-propagating, or far field radiation as well as for near-field radiation.

Figure 10A:
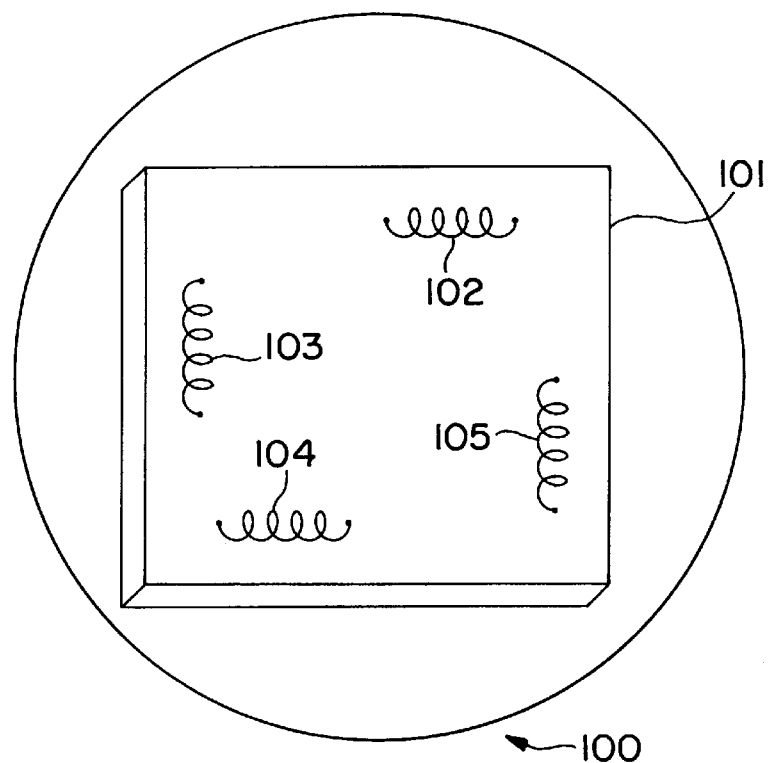
Figs. 10a–d are perspective views of different multiple leg antenna configurations in accord with this invention.
Figure 10B:
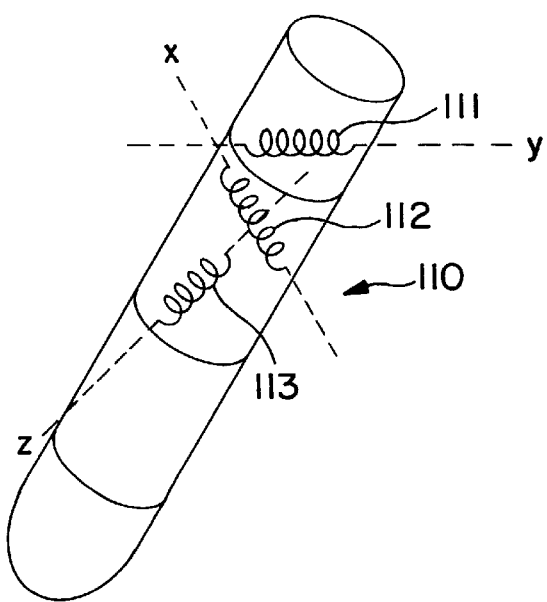
Figure 10C:
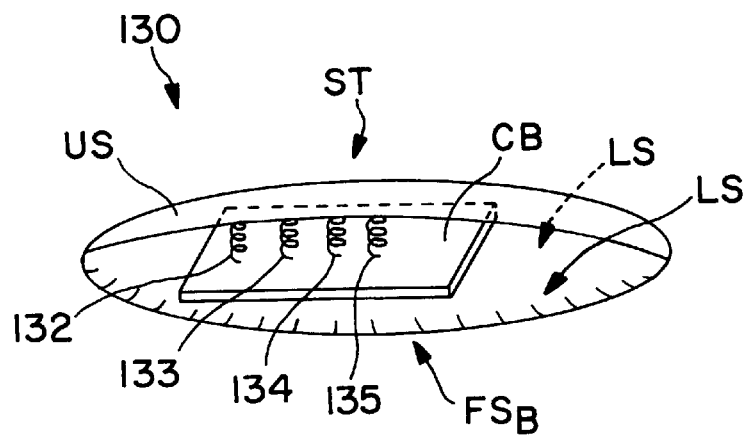

It should also be realized that the ideas presented above can be applied to many different configurations of antenna legs and device shapes. In FIG. 10a, a roundish flat device 100 has a circuit board (sometimes called a hybrid circuit board or just hybrid) 101 onto the surface plane of which are mounted four coil legs 102–105. Although it is unclear how such an arrangement's sweet spot configuration which would radiate best out from and essentially in the plane of the hybrid would be advantageous in an implantable device, it is not an arrangement excluded from the scope of this invention. Of more efficacy would be a device with antenna leg configuration as shown in FIG. 10b, where the device 110 is a bullet shaped or round device, that, if inserted close to a body's surface under the skin, may be lodged in the body in any orientation. The axis of one of the antennae 111–113 is likely to be near perpendicular to the skin surface and to produce a sweet spot radiating linear to directly out from the body. If a device such as device 130 pictured in FIG. 10c is contemplated, having a large surface area flat surface FIB on the 'bottom' of the device and a relatively flat top surface PST (having a broken skin US, sectioned here to show the lower interior surface LS, it may, for some applications be useful to concentrate the sweet spot by putting all the antenna legs 132–135 in a row on the circuit board CB. Thus it should be clear that the exact number and the orientation of the legs may be adapted to suit the user's need without deviating from the scope of this invention.

Additionally, if the sweet spot is extended sufficiently, a patient having a device implanted within him may take advantage of this in the following manner. The device may report out information from the device to a communications device similar to the programming head and programming unit of FIG. 1. This similar device could then, either through wireless telephony or through wired lines to the telephone system, report such information to an attending medical community that is caring for such a patient. With the additional range of the sweet spot enhancing invention described herein, the patient may possibly avoid having to wear such a device and the mere presence of the communications device in his room at night when he sleeps should be sufficient to place it in the range of the telemetry of the implant. Of course two way communication or activation is inherent in this concept.

Figure 10D:
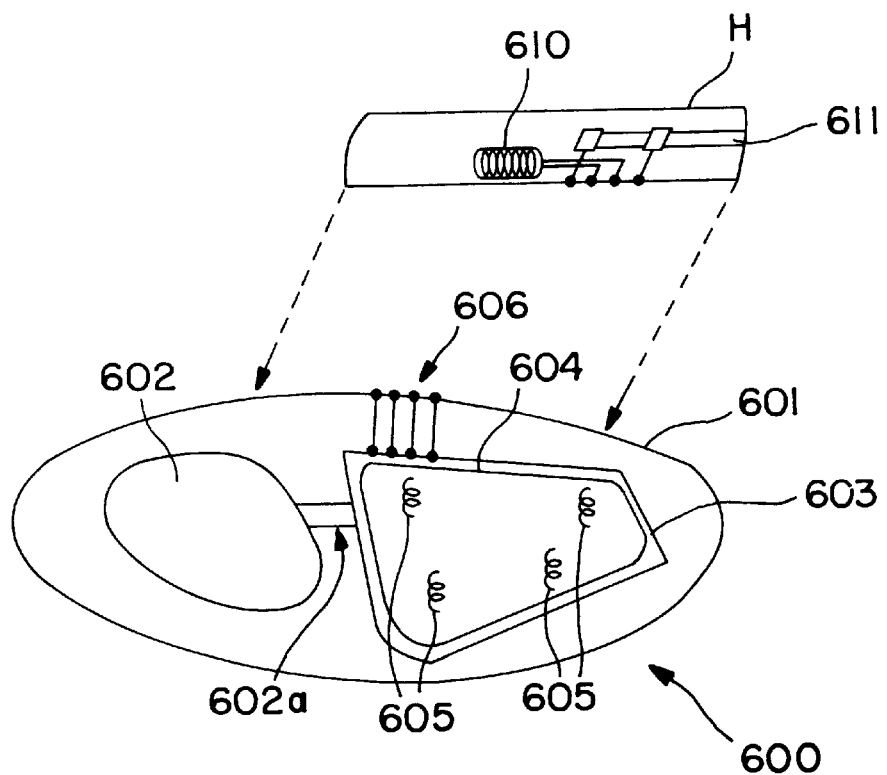

Additionally, it may in some circumstances be useful to employ a mixed system, having a single large air-core antenna and a multi-leg antenna as described above. An example can be seen illustrated in FIG. 10d where a device 600 which is here shown with an opened housing 601 containing the main pieces including the power source, battery 602, connected to a hybrid circuit board 603 by electrical conductors 602a. On the surface of the hybrid 603, is mounted a large air core antenna 604 around the periphery of the hybrid and the multi-leg antenna at locations indicated by numeral 605. In such a configuration the designer has the opportunity to employ the large air core antenna for receiving transmissions to the implanted device 600 and also employing the antenna at locations 605 for outbound transmissions. Also shown in FIG. 10d are conductors 600 electrically connecting the hybrid 603 to the outside surface of the implant housing 601). Use could be made of either internal antenna system (605's or 604 or both) together with an external antenna 610 in a connector block or header H (having a connecting lead bore 611) if desired so that additional flexibility in the types of signal transmissions to and from the implantable device may be had.

The detailed description outlined above is considered to be illustrative only of the principles of the invention. Numerous changes and modifications will occur to those skilled in the art, and there is no intention to restrict the scope of the invention to the detailed description. The preferred embodiments of the invention having been described in detail the scope of the invention should be defined by the following claims.

What is claimed is:

1. An implantable medical device having an antenna apparatus, said medical device having a power source to supply a substantially fixed voltage, said antenna apparatus comprising:

a plurality of electrical elements connected in parallel and not in series with each other in an electrical circuit with said power source, each of said plurality of electrical elements comprising an antenna coil having a core therein and each said antenna coil and said core physically separated from each other antenna coil.

2. The device in claim 1 further comprising a modulating circuit for modulating a current signal provided by said power source to said plurality of electrical elements.

3. The device in claim 1 wherein said plurality of electrical elements is mounted within a housing of said implantable medical device, said housing comprised of biocompatible material.

4. The device in claim 3 wherein said housing comprises a hermetically sealed can.

5. The device in claim 3 wherein said housing substantially comprises titanium.

6. The device in accordance with claim 1, wherein the number of said electrical elements is more than 1 and less than 6.

7. The device in accordance with claim 1, wherein each:
said core comprises a non-conductive medium, around which said coil winds.

8. The device in accordance with claim 1, wherein each said core comprises ferrite, around which said coil winds.

9. The device in accordance with claim 1, wherein each said core comprises air, around which said coil winds.

10. An implantable medical device for use with an external programming unit having an external programming unit antenna; said external programming unit having uplink and downlink telemetry transceiver means for communicating with a complementary transceiver means in said implantable medical device, said implantable medical device comprising:

said complementary transceiver means comprising an antenna circuit and an antenna configuration comprising a plurality of spaced apart substantially identical antenna legs, said antenna legs having two ends each and said antenna legs being connected in parallel at both said ends to said antenna circuit without being connected to said antenna circuit through any of said plurality of antenna legs or any other antenna leg.

11. The implantable medical device of claim 10, wherein the number of said legs is greater than one and less than 10.

12. The implantable medical device of claim 10, wherein each antenna leg comprises a metal coil, wherein each leg has an axis aligned with the center of the coil, and wherein said aligned axis of each of the metal coil antenna legs is substantially parallel.

13. The implantable medical device of claim 10, wherein said antenna legs are equally spaced about said implantable medical device wherein substantially the largest possible sweet spot is produced.

14. The implantable medical device of claim 10, wherein said antenna legs are spaced about within said implantable medical device to enable the use of a telemetry sweet spot of a predetermined shape.

15. The implantable medical device of claim 10 wherein said antenna legs are spaced about within said implantable medical device to enable the use of a telemetry sweet spot which projects a maximum amount in a predetermined direction.

16. The implantable medical device of claim 10 wherein said electrical elements are spaced about within said implantable medical device to enable the use of a telemetry sweet spot with a range determined to include a space outside of a body into which said device is designed for implantation from more than a single implant orientation.

17. The implantable medical device of claim 10 wherein said antenna legs are spaced about within said implantable medical device to enable the use of a telemetry sweet spot which projects a sufficient amount to be within communication range of a communications device which may be in a fixed location relative to a likely location of a patient during said patient's normal living activities.

* * * * *